United States Patent
Himmler et al.

(12) 
(10) Patent No.: US 6,436,955 B1
(45) Date of Patent: Aug. 20, 2002

(54) CRYSTAL MODIFICATION A OF 8-CYANO-1-CYCLOPROPYL-7-(IS,6S-2,8-DIAZABICYCLO [4.3.0]NONAN-8-YL)-6-FLUORO-1,4-DIHYDRO-4-OXO-3-QUINOLINECARBOXYLIC ACID

(75) Inventors: Thomas Himmler, Odenthal; Werner Hallenbach, Monheim; Hubert Rast, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/856,669

(22) PCT Filed: Nov. 15, 1999

(86) PCT No.: PCT/EP99/08775

§ 371 (c)(1),
(2), (4) Date: May 23, 2001

(87) PCT Pub. No.: WO00/31075

PCT Pub. Date: Jun. 2, 2000

(30) Foreign Application Priority Data

Nov. 25, 1998 (DE) .......................... 198 54 356

(51) Int. Cl.⁷ .................. A61K 31/437; A61K 31/4709; C07D 471/04; A61P 31/02
(52) U.S. Cl. ........................ 514/300; 546/113
(58) Field of Search .................. 514/300; 546/113

(56) References Cited

U.S. PATENT DOCUMENTS 5,849,752 A * 12/1998 Grunenberg ............... 514/300
6,278,013 B1 * 8/2001 Bartel ........................ 558/415

FOREIGN PATENT DOCUMENTS

| DE | 19546240 | 6/1997 |
| DE | 19633805 | 8/1997 |
| WO | 96/16055 | 5/1996 |
| WO | 00/31076 | 6/2000 |
| WO | 00/52009 | 9/2000 |
| WO | 00/52010 | 9/2000 |

* cited by examiner

*Primary Examiner*—Evelyn Mei Huang
(74) *Attorney, Agent, or Firm*—Joseph C. Gil; Godfried R. Akorli

(57) ABSTRACT

The present invention relates to a defined crystal modification of 8-cyano-1-cyclopropyl-7-(1S,6S-2,8-diazabicyclo [4.3.0] nonan-8-yl)-6-fluoro-1, 4-dihydro-4-oxo-3-quinolinecarboxylic acid of the formula (I), to processes for its preparation and to its use in pharmaceutical preparations.

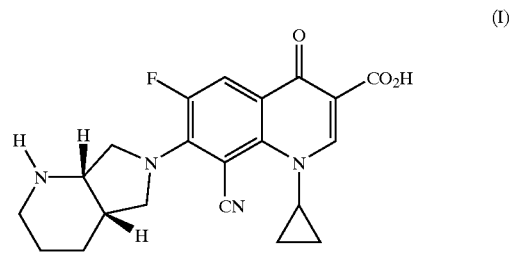

(I)

The crystal modification can be distinguished from other crystal modifications of 8-cyano-1-cyclopropyl-7-(1S,6S-2, 8-diazabicyclo[4.3.0]nonan-8-yl )-6-fluoro-1,4-dihydro-4-oxo-3-quinolinecarboxylic acid of the formula (I) by its characteristic X-ray powder diffractogram and its differential thermodiagram (see description).

11 Claims, 4 Drawing Sheets

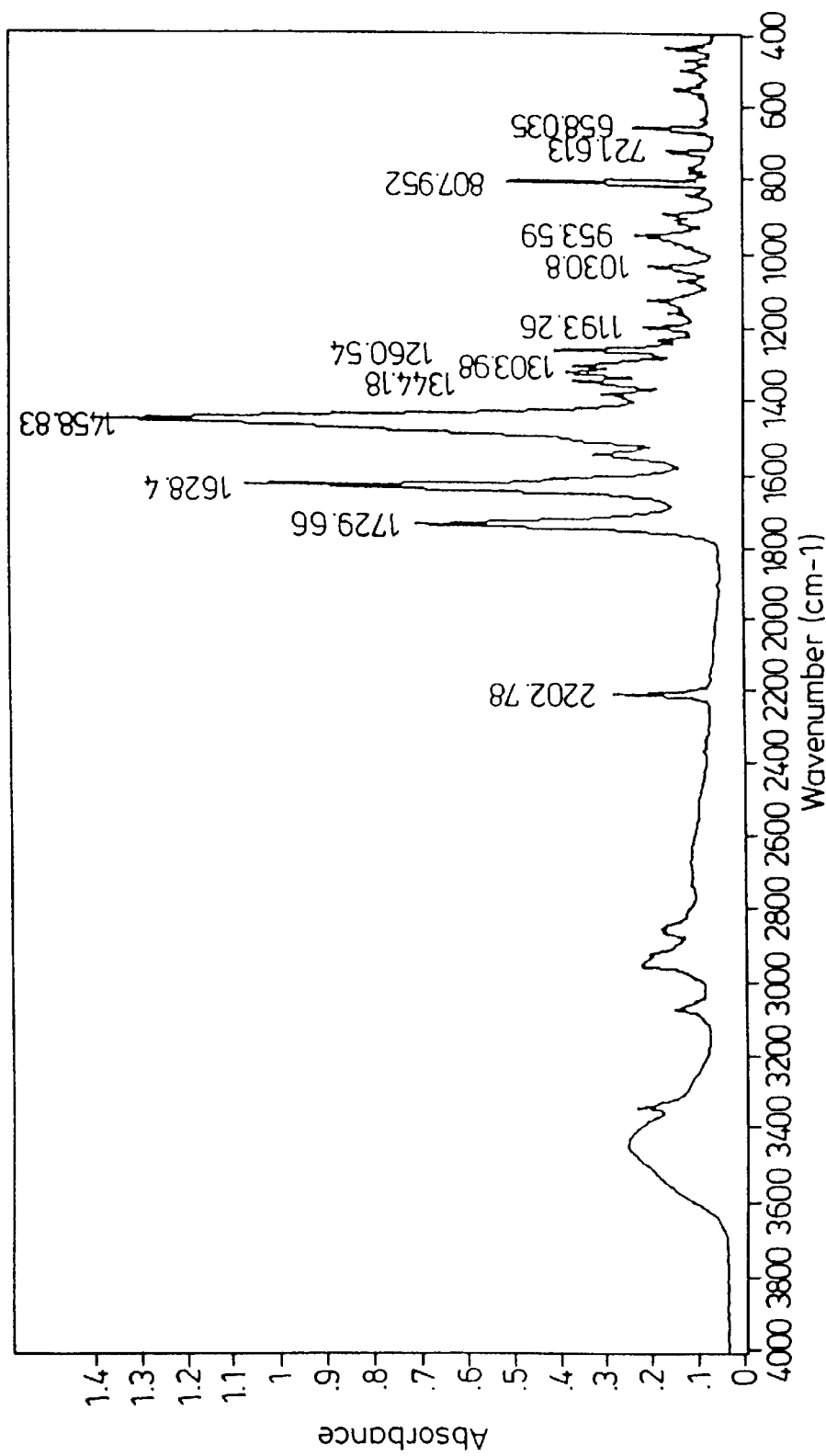
Fig. 3 Modifikation A

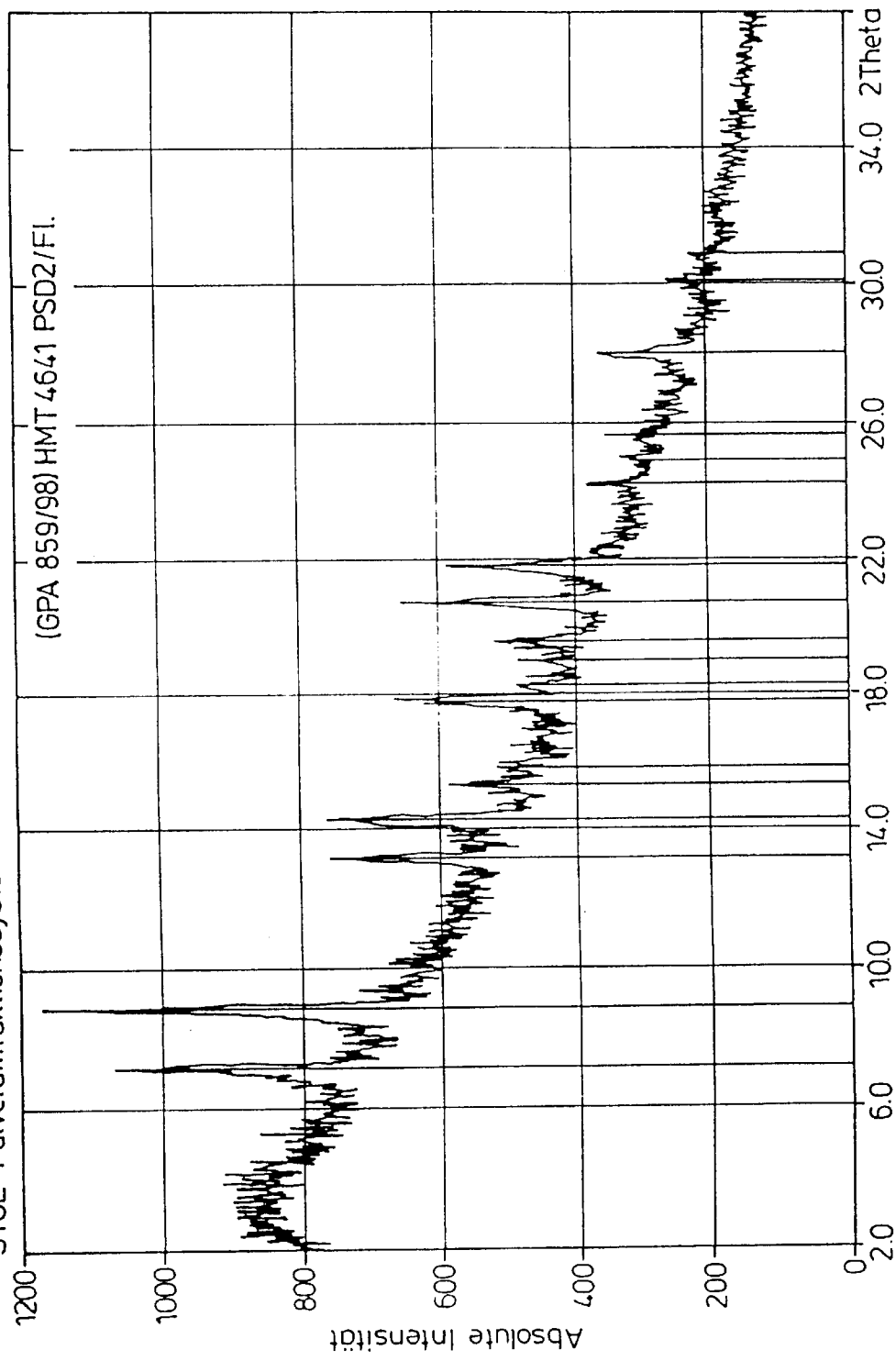

CRYSTAL MODIFICATION A OF 8-CYANO-1-CYCLOPROPYL-7-(1S,6S-2,8-DIAZABICYCLO[4.3.0]NONAN-8-YL)-6-FLUORO-1,4-DIHYDRO-4-OXO-3-QUINOLINECARBOXYLIC ACID

This application is the 371 of PCT/EP99/08775 filed on Nov. 15, 1999.

The present invention relates to a defined crystal modification of 8-cyano-1-cyclopropyl-7-(1S,6S-2,8-diazabicyclo[4.3.0]nonan-8-yl)-6-fluoro-1, 4-dihydro-4-oxo-3-quinolinecarboxylic acid, to processes for its preparation and to its use in pharmaceutical preparations.

Hereinbelow, 8-cyano-1-cyclopropyl-7-(1S,6S-2,8-diazabicyclo[4.3.0]nonan-8-y 1)-6-fluoro-1,4-dihydro-4-oxo-3-quinolinecarboxylic acid of the formula (I) is referred to as CCDC.

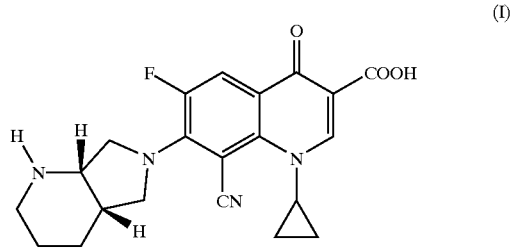

(I)

CCDC is known from DE-A 19 633 805 or PCT Appl. No. 97 903 260.4. According to these publications, it is prepared by reacting 7-chloro-8-cyano-1-cyclopropyl-6-fluoro-1,4-dihydro-4-oxo-3-quinolinecarboxylic acid with (1S,6S)-2,8-diaza-bicyclo[4.3.0]nonane in a mixture of dimethylformamide and acetonitrile in the presence of an auxiliary base. Water is added to the mixture and CCDC is then extracted from water using dichloromethane and is isolated by removing the extractant. This gives a powder whose crystal modification is not unambiguous. On the contrary, the powder is largely amorphous and can contain mixtures of different crystal modifications. If, by chance, a uniform crystal modification is formed, it is not clear how it can be extracted and obtained in a defined form. However, it is the precondition for preparing medicaments that, for an active compound which can be present in different crystal modifications, it can be stated unambiguously which of its crystal modifications is used for preparing the agent.

The partially amorphous powder, which is obtained by the preparation process outlined above, is furthermore hygroscopic. Amorphous solids, and in particular hygroscopic solids, are difficult to handle when being processed pharmaceutically since, for example, they may have low bulk densities and unsatisfactory flow properties. Moreover, the handling of hygroscopic solids requires special work techniques and apparatuses to obtain reproducible results, for example with respect to the active compound content or the stability of the solid formulations produced.

It is therefore an object of the invention to prepare a crystalline form of a defined modification of CCDC which, owing to its physical properties, in particular its crystal properties and its behaviour towards water, is easy to handle in pharmaceutical formulations.

This object is achieved according to the invention by a novel crystalline form of CCDC which is referred to as modification A hereinbelow.

BRIEF DESCRIPTION OF DRAWINGS

A characteristic X-ray powder diffractogram of the CCDC of modification A is shown in FIG. 1.

A characteristic differential thermodiagram CCDC of the modification A is shown in FIG. 2.

An infrared spectrum of CCDC of the modification A, measured in KBr, is shown in FIG. 3.

An X-ray powder diffractogram of the CCDA obtained by the Comparative Example at page 5 is shown in FIG. 4.

The invention accordingly provides the crystalline modification A of CCDC which is characterized by an X-ray powder diffractogram having the reflection signals (2 theta) of high and medium intensity (>30% relative intensity) listed in Table 1 below.

TABLE 1

X-ray powder diffractogram of CCDC of the modification A

| 2 θ (2 theta) |
|---|
| 6.70 |
| 8.92 |
| 12.44 |
| 13.66 |
| 15.96 |
| 17.60 |
| 21.42 |
| 21.78 |
| 28.97 |

Figure 1:
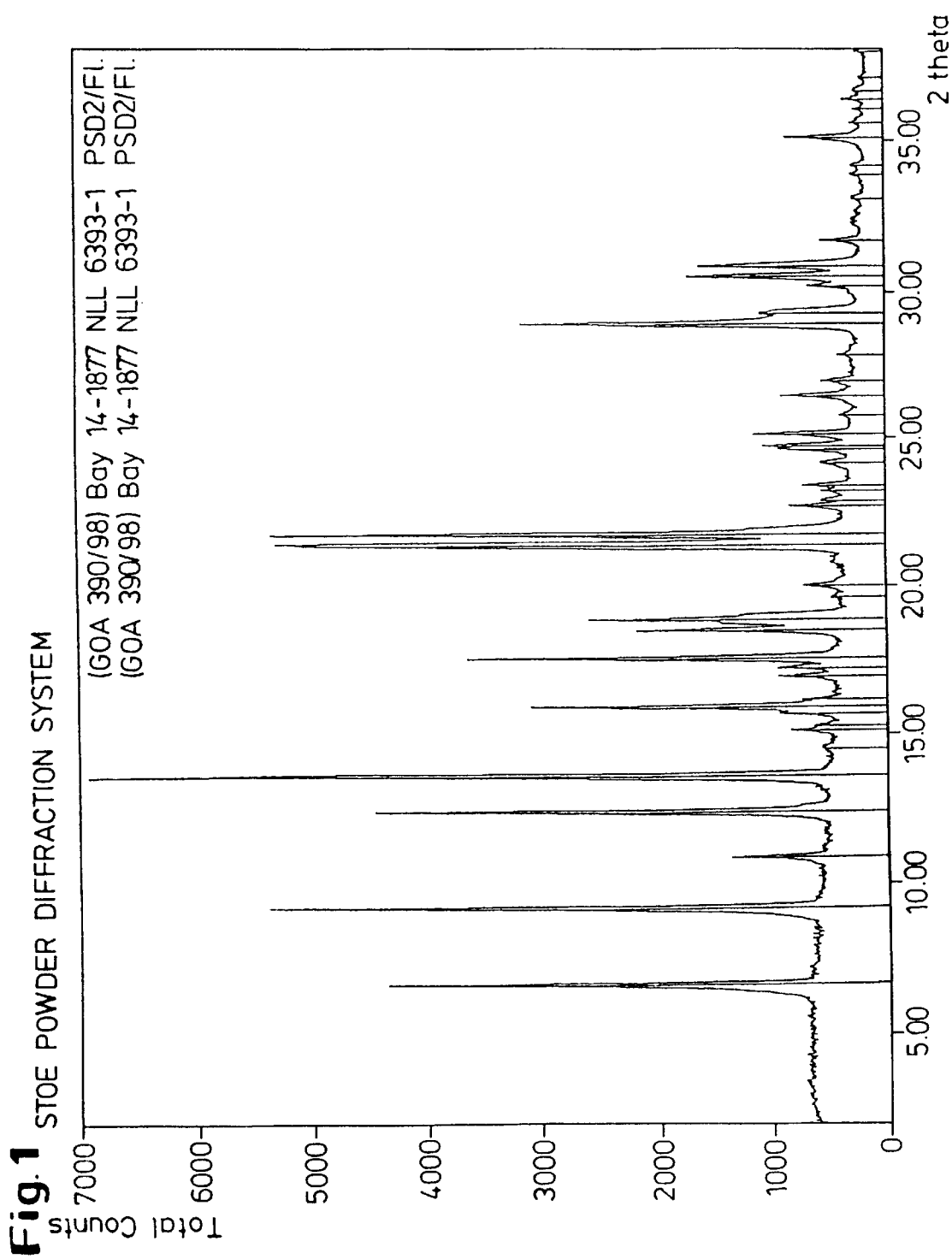

A characteristic X-ray powder diffractogram of the modification A is also shown in FIG. 1.

Moreover, the CCDC modification A according to the invention differs from other forms of CCDC in a number of further properties. These properties, on their own or together with the other parameters, may serve for characterizing the CCDC modification A according to the invention.

Figure 2:
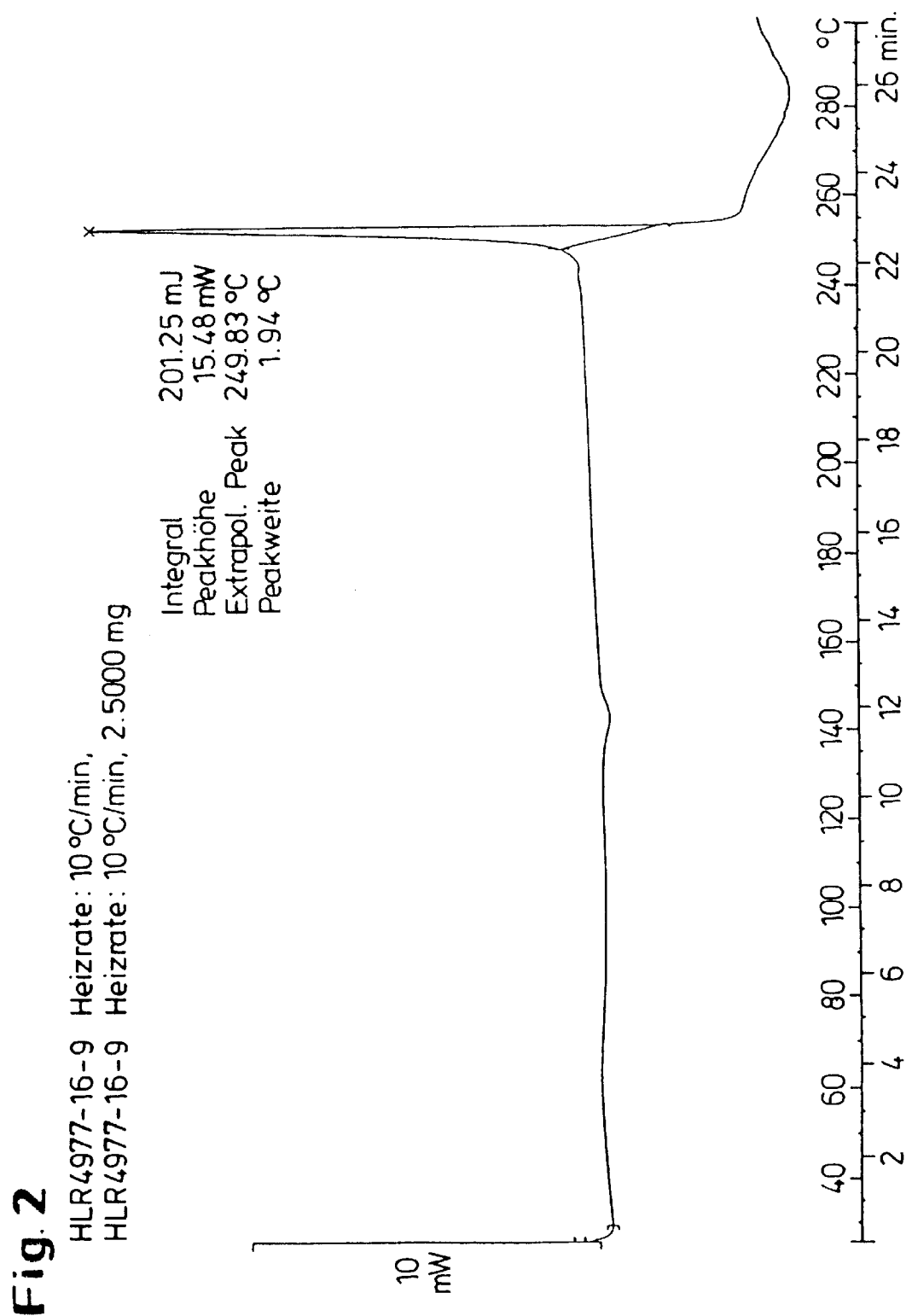

The CCDC of the modification A is, inter alia, characterized by a melting point, determined with the aid of differential thermoanalysis (DTA), of from 249 to 252° C. A characteristic differential thermodiagram is shown in FIG. 2.

CCDC of the modification A is also characterized in that it has an infrared spectrum, measured in KBr, as shown in FIG. 3.

CCDC of the modification A is furthermore characterized in that it is obtainable by the preparation process given below. The crystal modification A of CCDC is obtained by dissolving CCDC of unknown modification or amorphous CCDC in hot water or a hot alcohol/water mixture, subsequently adding an alcohol and, after cooling to room temperature, isolating the precipitated solid.

In a preferred embodiment, the alcohol used is ethanol or isopropanol.

CCDC of the crystal modification A is surprisingly stable and does not change into another crystal modification or the amorphous form, even on prolonged storage. In addition, compared with amorphous CCDC, the modification A tends to absorb much less water from the atmosphere. For these reasons, it is highly suitable for preparing tablets or other solid formulations. Owing to its stability, it gives these formulations the desired long-lasting storage stability. Using the crystal modification A, it is therefore possible to prepare, in a defined and targeted manner, stable solid preparations of CCDC.

CCDC of the crystal modification A is highly active against pathogenic bacteria in the field of human or veterinary medicine. Its broad area of use corresponds to that of CCDC.

The X-ray powder diffractogram for characterizing the crystal modification A of CCDC was obtained using a transmission diffractometer STADI-P with a location-sensitive detector (PSD2) from Stoe.

The melting point of the differential thermoanalysis was obtained using the DSC 820 unit from Mettler-Toledo. Here, the sample of CCDC of the crystal modification A was heated exposed to the atmosphere in an aluminium crucible at 10 K/min.

The KBr IR spectrum was obtained using the FTS 60A unit from Biorad.

The examples below illustrate the invention without limiting it. The solvent/base systems used in the examples below are particularly preferred.

Comparative Example

A mixture of 3.07 g of 7-chloro-8-cyano-1-cyclopropyl-6-fluoro-1, 4-dihydro4-oxo-3-quinolinecarboxylic acid, 1.39 g of (1S,6S)-2,8-diazabicyclo[4.3.0]nonane, 2.24 g of (hot precipitation) 1,4-diazabicyclo[2.2.2]octane (DABCO), 29.5 ml of dimethylformamide and 29.5 ml of acetonitrile is stirred at room temperature for 16 hours. The reaction mixture is concentrated at a bath temperature of 60° C. using a rotary evaporator, and the residue is taken up in 10 ml of water. The resulting solution is adjusted to pH 7 using dilute hydrochloric acid, and the solid is filtered off. The filtrate is extracted three times using 20 ml of dichloromethane each time. The organic phase is dried over sodium sulphate and filtered and the filtrate is concentrated at a bath temperature of 60° C. using a rotary evaporator. This gives 2.4 g of a light-brown solid which has the X-ray powder diffractogram shown in FIG. 4 and is therefore predominantlyamorphous.

At a relative atmospheric humidity of 95% (established using a saturated solution of $Na_2HPO_4 \times 12\ H_2O$ with sediment in water), the solid obtained according to this procedure absorbs approximately 17% by weight of water within one day.

Example 1

617 g of CCDC of any modification are dissolved in 6170 ml of chloroform. 100 g of sodium sulphate are added, the mixture is stirred for 5 minutes and then filtered through 50 g of kieselguhr, which is then washed with 100 ml of chloroform. The solvent is distilled off on a rotary evaporator up to a residual pressure of 10 mbar, resulting in a glass-like residue. 740 ml of water and 740 ml of ethanol are added to this residue, and the mixture is heated at 60° C. until the entire residue has been dissolved. This solution is then added to 17 liters of boiling ethanol. This mixture is boiled for a further 5 minutes and then cooled to 35° C. over a period of one hour. The precipitated crystals are filtered off with suction and dried at 20° C. for approximately 16 hours and then at 30° C. under reduced pressure until the weight remains constant.

This gives 530 g of a solid which has the X-ray powder diffractogram shown in FIG. 1, the differential thermodiagram shown in FIG. 2 and the IR spectrum shown in FIG. 3.

At a relative atmospheric humidity of 95% (established using a saturated solution of $Na_2HPO_4 \times 12\ H_2O$ with sediment in water), the solid obtained according to this procedure absorbs approximately 3% by weight of water within one day.

Example 2

2 g of CCDC of unknown modification are dissolved in 4 ml of water. 4 ml of isopropanol are added, the reaction mixture is slowly heated with stirring and a further 32 ml of isopropanol are then added. The resulting clear solution is brought to the boil. The solution becomes turbid, and within a short period of time, crystals precipitate out. After 3 minutes at reflux, the heating is removed and the mixture is allowed to stand without stirring for 3 to 4 hours. The solid is then filtered off with suction, washed with isopropanol and dried in the atmosphere until the weight remains constant. This gives 1.54 g of a solid which has an X-ray powder diffractogram identical to that shown in FIG. 1, a differential thermodiagram identical to that shown in FIG. 2 and an IR spectrum identical to that shown in FIG. 3.

What is claimed is:

1. 8-Cyano-1-cyclopropyl-7-(1S,6S-2,8-diazabicyclo[4.3.0]nonan-8-yl)-6-fluoro-1,4-dihydro4-oxo-3-quinolinecarboxylic acid (CCDC) of the crystal modification A, having an X-ray powder diffractogram with the following reflection signals (2 theta) of high and medium intensity

| 2 θ (2 theta) |
| --- |
| 6.70 |
| 8.92 |
| 12.44 |
| 13.66 |
| 15.96 |
| 17.60 |
| 21.42 |
| 21.78 |
| 28.97. |

2. 8-Cyano-1-cyclopropyl-7-(1S,6S-2,8-diazabicyclo[4.3.0]nonan-8-yl)-6-fluoro-1,4-dihydro-4-oxo-3-quinolinecarboxylic acid (CCDC) of the crystal modification A, having an X-ray powder diffractogram with the following reflection signals (2 theta) of high and medium intensity

| 2 θ (2 theta) |
| --- |
| 6.70 |
| 8.92 |
| 12.44 |
| 13.66 |
| 15.96 |
| 17.60 |
| 21.42 |
| 21.78 |
| 28.97 | and a melting point, determined by DTA, of from 249° C. to 252° C.

3. 8-Cyano-1-cyclopropyl-7-(l1S,6S-2,8-diazabicyclo[4.3.0]nonan-8-yl)-6-fluoro-1,4-dihydro-4-oxo-3-quinolinecarboxylic acid (CCDC) of the crystal modification A as recited in claim 1 or 2, obtainable by dissolving CCDC of unknown modification or amorphous CCDC in water or a water/alcohol mixture, followed by hot precipitation after the addition of alcohol.

4. Process for preparing CCDC of the modification A according to claim 1, comprising dissolving CCDC of unknown modification or amorphous CCDC in water or a water/alcohol mixture, adding alcohol to the resulting mixture and hot precipitating the CCDC of the modification A.

5. Process for preparing CCDC of the modification A according to claim 4, wherein the alcohol used is ethanol or isopropanol.

6. A method of preparing a composition comprising formulating CCDC of the modification A according to claim 1.

7. A process for combating bacteria comprising admiunistering to the manual in need thereof amount of CCDC of the modification A according to claim 1.

8. A method of preparing a composition comprising formulating CCDC of the modification A according to claim 2.

9. A method of preparing a composition comprising formulating CCDC of the modification A according to claim 3.

10. A process for combating bacteria comprising administering to a manual in used thereof an antibacterial amount of CCDC of the modification A according to claim 2.

11. A process for combating bacteria comprising administering to a manual in need thereof an antibacterial amount of CCDC of the modification A according to claim 3.

* * * * *

UNITED STATES PATENT AND TRADEMARK OFFICE
CERTIFICATE OF CORRECTION

PATENT NO.     : 6,436,955 B1
DATED          : August 20, 2002
INVENTOR(S)    : Thomas Himmler, Werner Hallenbach and Hubert Rast It is certified that error appears in the above-identified patent and that said Letters Patent is hereby corrected as shown below:

Column 5,
Line 7, delete "admiunistering" and replace with -- administering --;
Line 8, delete "the manual" and replace with -- a mammal --;
Line 8, after "thereof" insert -- an antibacterial --.

Column 6,
Line 5, delete "manual" and replace with -- mammal --;
Line 5, delete "used" and replace with -- need --.
Line 9, delete "manual" and replace with -- mammal --.

Signed and Sealed this

Twenty-second Day of July, 2003

JAMES E. ROGAN
*Director of the United States Patent and Trademark Office*